DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED OCTOBER 13, 1970

879 O.G. 366

T879,008

METHOD FOR PREPARING ISOXAZOLIUM SALTS

Donald M. Burness and Victor O. Stead, both % Kodak Park Works, Rochester, N.Y. 14650

Filed Apr. 20, 1970, Ser. No. 30,309
Int. Cl. C07d *85/22*
U.S. Cl. 260—307
No Drawing. 7 Pages Specification

Tetramethylene sulfone (sulfolane) or an alkyl-substituted derivative thereof such as 3-methylsulfolane when used as the reaction solvent in the quaternization of isoxazoles with alkylation agents to isoxazolium salts has been found to reduce reaction times and by-products formation and to minimize purification problems. The quaternization can be carried out at temperatures of about 20° C. to 250° C., preferably at about 40° C. to 100° C. 2-ethyl - 5 - methylisoxazolium ethosulfate, for example, was prepared by heating a solution of 25 grams of 5-methylisoxazole, 61 grams of diethyl sulfate and 15 grams of tetramethylene sulfone at 50° C. for 66 hours and recovering the desired product as a yellow oil from the reaction mixture.